United States Patent
Gibbs et al.

[11] Patent Number: 6,099,303
[45] Date of Patent: Aug. 8, 2000

[54] FORCE RECORDING ORTHODONTIC APPLIANCE

[75] Inventors: Charles H. Gibbs, Gainesville; Stephen Keeling, deceased, late of Gainesville, by Marilyn Keeling, legal representative; Glenn S. Dean, Gainesville; Yossi Bar-Zion, Gainesville; Hoyt Howard Plumley, Jr., Gainesville, all of Fla.

[73] Assignee: University of Florida, Gainesville, Fla.

[21] Appl. No.: 09/240,869

[22] Filed: Feb. 1, 1999

[51] Int. Cl.[7] ................................................. A61C 3/00
[52] U.S. Cl. ................................................. 433/5
[58] Field of Search ................................................. 433/5

[56] References Cited

U.S. PATENT DOCUMENTS

| | | | |
|---|---|---|---|
| 3,533,163 | 10/1970 | Kirschenbaum | 433/5 |
| 3,765,093 | 10/1973 | DeWoskin | 433/5 |
| 3,885,310 | 5/1975 | Northcutt | 433/5 |
| 3,900,953 | 8/1975 | Posen | 433/72 |
| 4,081,996 | 4/1978 | Jennings et al. | 73/141 A |
| 4,228,591 | 10/1980 | Sterki et al. | 33/174 L |
| 4,478,580 | 10/1984 | Barrut | 433/223 |
| 4,825,701 | 5/1989 | Holtslander | 73/782 |
| 5,651,671 | 7/1997 | Seay et al. | 433/5 |
| 5,980,246 | 11/1999 | Ramsay et al. | 433/5 |

*Primary Examiner*—John J. Wilson
*Attorney, Agent, or Firm*—Miles & Stockbridge; Dennis P. Clarke

[57] ABSTRACT

A removable orthodontic appliance includes a first force applicator spring and a data storage device that stores data corresponding to the force being applied by the spring. A potentiometer serves as a force measurer to indicate the magnitude of the extra-oral corrective forces applied to the teeth of a patient. A bending switch is operable connected between the potentiometer and the data storage device. The bending switch indicates whether the appliance is on a patient by sensing whether it is bent.

19 Claims, 3 Drawing Sheets

FORCE RECORDING ORTHODONTIC APPLIANCE

BACKGROUND OF THE INVENTION

1. Field of the Invention

The present invention relates to removable orthodontic appliances that exert corrective forces on teeth.

2. Description of the Prior Art

Orthodontics is a specialty of dentistry which is concerned with the treatment of malpositioned teeth and the correction of improper relationships of the teeth and dental arches. It is common to utilize extra-oral orthodontic appliances to correct improperly positioned teeth. It is also common in extra-oral appliances to use some form of elastic mechanism so that a force can be applied to the teeth.

Headgear assemblies are commonly used in orthodontic treatment to apply forces to a patient's teeth to accomplish specific types of tooth movements. Such headgear assemblies typically include an inner bow, an outer bow and some type of a neck/head strap assembly. More particularly, the two ends of the inner bow are each typically inserted into a buccal tube attached to one of the upper first molars. Moreover, the outer bow is connected to the inner bow and extends at least partially about both sides of the patient's face such that the ends of the outer bow may be engaged by the neck/head strap assembly. The neck/head strap assembly is generally formed at least in part from an elastic material or other energy-storing mechanism so as to be capable of stretching and, thus, applying the desired treatment forces to each of the ends of the outer bow. These treatment forces are then typically transmitted to the upper first molars and any teeth interconnected therewith (e.g., via an arch wire and/or other appropriate connectors).

The most common type of force producing device is the coil spring. Coil springs that have been commonly used in the past are stainless steel springs. The advantage of springs as a force producing device is that they almost never require replacement during the entire length of time of usage. The disadvantage of most springs that are in common use is that they do not apply a constant force over different deflections. Deflection increases and decreases when the user speaks or moves his or her head. Therefore, when using the conventional stainless steel type of spring, the force that is applied is constantly changing. Orthodontists feel that constant force application moves the teeth more efficiently than variable forces. Furthermore, variable forces can cause pain, especially if the force significantly increases momentarily.

Moreover, to be effective, an orthodontic device must be worn over an extended period of time each day. In addition, orthodontists, in many cases, guarantee that they will be able to align a patient's teeth. For both purposes, it is desirable to record how long a patient actually wears an orthodontic device and the amount of extra-oral force exerted.

The use of removable appliances that exert corrective forces on teeth such as headgears, mono-blocks, activators, crozats, retainers, spring-loaded retainers and the like is at the discretion of the patient who most often is an adolescent. Since the appliance may be somewhat uncomfortable and inconvenient to wear, it takes considerable will power to adhere to a treatment program. It can be particularly difficult to adhere to a program for an adolescent who may not fully recognize the true value of the treatment.

The rate of corrective movement of teeth is a function both of the forces applied to the teeth and the amount of time those forces have been applied. Failure to wear an appliance for the prescribed periods results in reduced corrective movement of the teeth and, in addition, such failure can result in the use of incorrect forces in later stages of the treatment. As treatment progresses, forces are often determined in relation to the effectiveness of forces used in earlier stages. If a patient represents that the program has been fully complied with when, in fact, it has not, the orthodontist is led to believe that the forces applied earlier were insufficient to cause the desired rate of tooth movement. As a consequence, excessive forces may later be chosen which can work to the detriment of the patient.

It is an object of the present invention to provide an orthodontic care device capable of applying an extra-oral force to a patient's jaw/teeth and of recording the force applied thereto as a function of the amount of time the device is actually worn.

Another object of the invention is to provide a memory read-out unit capable of reading the force/time history recorded by said orthodontic care device and storing such history, possibly with other previously stored force/time histories, for future retrieval.

An additional object of the invention is to provide means, such as a serial or parallel port, for down-loading information stored in the memory read-out unit into a computer so that the information can be analyzed, utilizing a suitable computer program, and printed out in a convenient format for review by an orthodontist and his patients.

SUMMARY OF THE INVENTION

The above and other objects are realized by a removable orthodontic appliance including at least one force applicator operable to exert extra-oral, corrective forces on teeth. A data storage device is operably connected to store data corresponding to force applied by the force applicator. A potentiometer is operably connected to the force applicator such that a resistance across two terminals of the potentiometer depends on the force being applied by the force applicator. The potentiometer is operably connected to supply a force signal to the data storage device such that the data storage device stores data corresponding to force applied by the force applicator. The potentiometer is a slide potentiometer having a slide member that moves dependent on the force applied by the force applicator. The force applicator is a first spring and the first spring is linked to the slide member such that the slide member moves dependent on the spring position. A second spring also applies the extra-oral, corrective forces. The first spring is biased in compression for applying the extra-oral, corrective forces.

A switch is operably connected between the data storage device and the potentiometer. The switch has a state (i.e., open or closed) dependent on whether the appliance is being worn by a patient. The state of the switch allows the data storage device to record patient compliance data indicating whether a patient is wearing the appliance.

The switch is in a closed state when the appliance is being worn by a patient and the switch is in an open state when the appliance is not being worn by a patient.

The switch is a bending switch that senses whether the appliance is on a patient by sensing whether it is bent.

The present invention may alternately be described as a removable orthodontic appliance including at least one force applicator operable to exert extra-oral, corrective forces on teeth; a data storage device operably connected to store data corresponding to force applied by the force applicator. A force measurer is operably connected to the force applicator. The force measurer is operably connected to supply a force signal to the data storage device such that the data storage device stores data corresponding to force applied by the force applicator. A switch is operably connected between the data storage device and the force measurer. The switch has a state dependent on whether the appliance is being worn by a patient. The state of the switch allows the data storage device to record patient compliance data indicating whether a patient is wearing the appliance. The switch is in a closed state when the appliance is being worn by a patient and the switch is in an open state when the appliance is not being worn by a patient. The switch is a bending switch that senses whether the appliance is on a patient by sensing whether it is bent. The force applicator is a first spring and the first spring is linked to move part of the force measurer. A second spring applies the extra-oral, corrective forces. The force measurer is a slide potentiometer having a slide and the slide is the part linked to the first spring. A resistance across two terminals of the potentiometer depends on the force being applied by the first spring. The potentiometer is operably connected to supply a force signal to the data storage device such that the data storage device stores data corresponding to force applied by the first spring. The slide is linked to move with the force applicator.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION OF THE INVENTION

Figure 1:
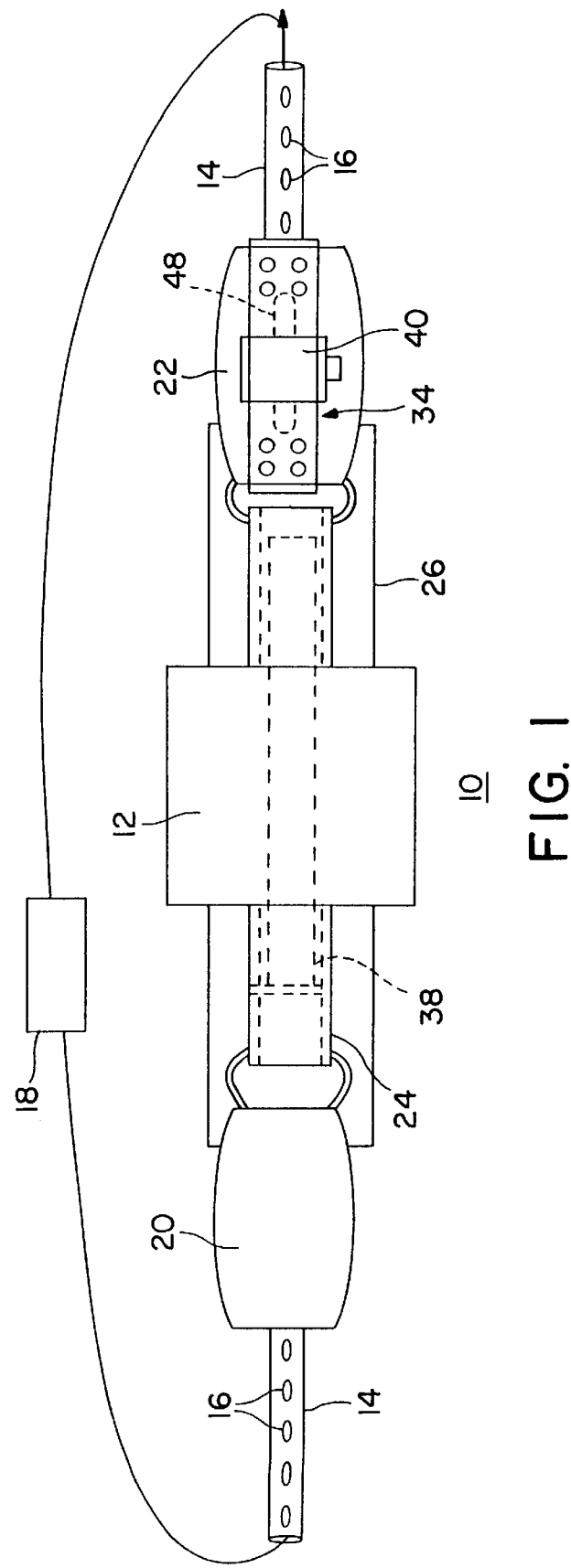
FIG. 1 is a simplified top view of the present invention.

The orthodontic appliance 10 according to the present invention is shown in FIG. 1. A data storage device 12, which may for example be an Onset Computer Corporation (Pocasset, Mass.) data logger device sold under the Stow-Away trademark, is used to record the force that is applied by the appliance to the patient's teeth. The device 12 can interface with a computer (not shown) in known fashion to transfer stored data to the computer for viewing and printing.

The appliance 10 has plastic straps 14 at each end, each plastic strap having holes 16 spaced along its length. The holes 16 allow attachment of an arch wire 18 (schematically illustrated only) such that the proper force will be applied to the patient's teeth (not shown). The plastic straps 14 are movably connected via spring housings 20 and 22 to a band 24 made of nylon or other fabric. A fabric pad 26 is connected to the neckband 24 to pad or cushion the band 24 and data storage device 12 from the back of a patient's neck.

The appliance 10 is used by having the holes 16 attached to an arch wire 18 such that springs (not visible in FIG. 1) within spring housings 20 and 22 apply corrective force to the patient's teeth (not shown). The straps 16 extend from the back of a patient's neck towards the patient's mouth on opposite sides of the patient's face. Band 24 serves as a neckband at the back of a patient's neck.

Figure 2:
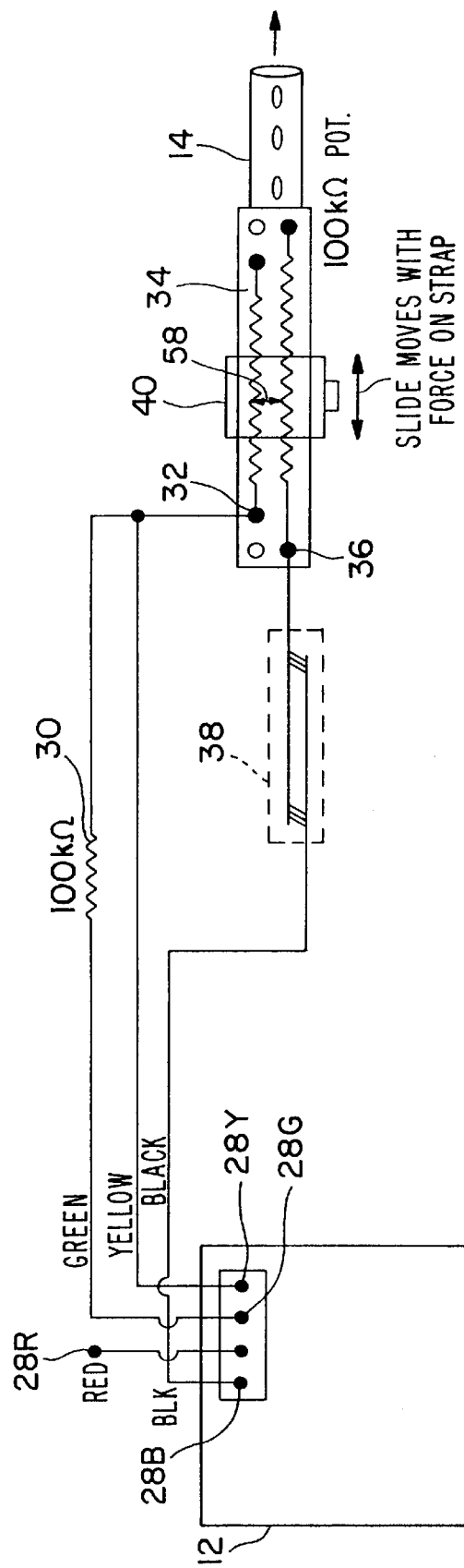
FIG. 2 is a simplified schematic of the present invention.

Continuing to view FIG. 1, but also considering the electrical schematic of FIG. 2, the device 12 has an internal battery (not shown) and four terminals 28B, 28R, 28G and 28Y. In the preferred embodiment, the four terminals may be respectively connected to black, red, green and yellow wires. Terminal 28B is the ground, terminal 28R is a battery output from device 12 which is not connected in the present design, terminal 28G is a battery supply that powers the potentiometer, and terminal 28Y is the "input sample" line that reads the voltage output from the potentiometer into device 12. The device 12 stores a digital representation of the difference between the voltage at "input sample" terminal 28Y and ground terminal 28B. This difference is stored at regular intervals such as once per minute.

Terminal 28G is connected to the terminal 28Y via 100 K resistor 30. The side of resistor 30 that is not connected to terminal 28G is also connected to terminal 32 of a slide potentiometer 34. Terminal 36 of potentiometer is connected to terminal 28B via a bending switch 38.

The details of potentiometer 34 will be discussed below with reference to FIGS. 3 and 4. Briefly, a slide 40 varies the resistance between terminals 32 and 36 depending on the position of slide 40. In turn, slide 40 moves as a function of the corrective force that the appliance 10 is applying to the patient's teeth. Accordingly, the voltage sensed across terminals 28B and 28Y depends on the position of slide 40 and the force applied by the appliance 10.

Figure 3:
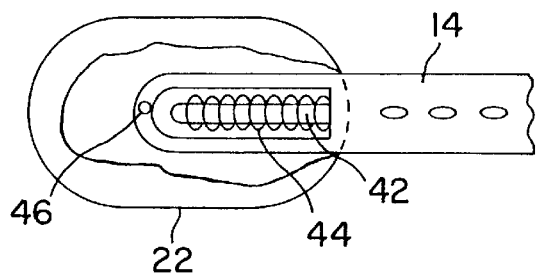
FIG. 3 is a top view, with portions broken away, of a spring housing and related parts.
Figure 4:
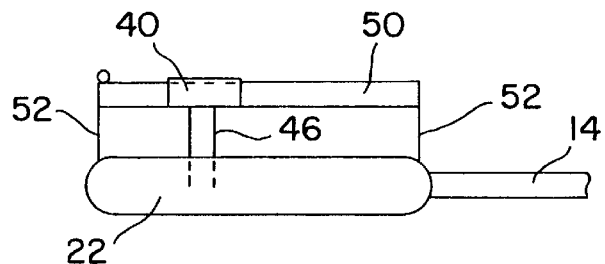
FIG. 4 is a side view of a spring housing, slide potentiometer and related parts.
Figure 5:
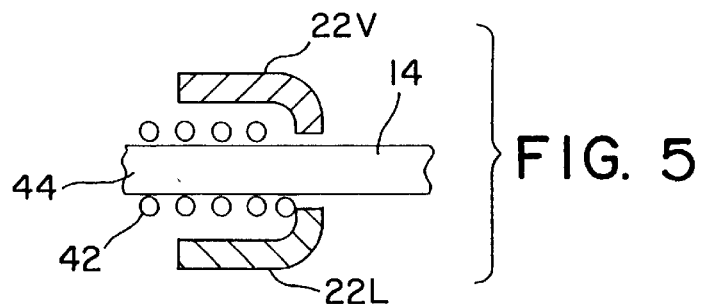
FIG. 5 is a side view of a spring housing, with parts in cross-section and related parts.

Turning now to FIGS. 3, 4 and 5, the construction of spring housing 22 and potentiometer 34 will be discussed in detail. Spring housing 22 holds a tongue 44 of strap 14 and a coil spring 42 around the tongue 44. The spring 42 biases the strap 14 in the leftward direction in FIGS. 3 and 4 as the top and bottom of the right side of spring 42 is trapped by upper and lower pieces 22U and 22L (FIG. 5 only) of housing 22, thus trapping the left end of strap 14 in FIG. 3.

A pin 46 (FIG. 3 only) extends up from the trapped end of strap 14 through a channel 48 (see phantom lines in FIG. 1 only). The pin is attached to slide 40 such that slide 40 moves along member 50 (movement is left and right in FIG. 4) offset from housing 22 by mount offsets 52.

Note that spring housing 20 (FIG. 1 only) is constructed in the same fashion as housing 22 with the same components therein except that pin 46 and channel 48 are not needed as the slide potentiometer 34 is used at one of the two straps 14 only.

Figure 6:
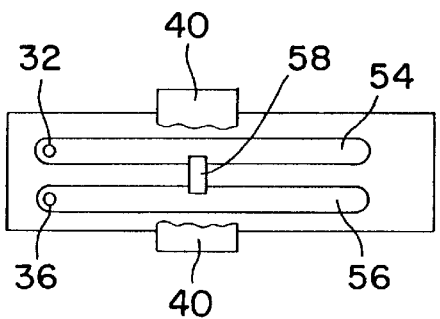
FIG. 6 is a top view of parts of a slide potentiometer, with portions broken away.

As shown in FIG. 6, one side of member 50 has two patches of resistive coating 54 and 56 respectively connected to terminals 32 and 36. The slide 40, portions of which are broken away in FIG. 6, has a connecting strip 58. The connecting strip 58 connects terminals 32 and 36 via a variable portion of coating patches 54 and 56. Therefore, the resistance between terminals 32 and 36 depends on the position of strip 58. As strip 58 is part of slide 40, the resistance varies with the movement of slide 40 and, in turn, the force applied by spring 42.

Advantageously, the bending switch 38, which may be a flex action ribbon switch 180-S as made by Tapeswitch Corporation (Farmingdale, N.Y.), is closed only when the switch is bent. As the switch 38 is in the band 24 (or between band 24 and pad 26), the switch 38 is closed when the patient is wearing the appliance 10. Conversely, when the patient is not wearing the appliance 10, the switch 38 is open.

This switch 38 allows the device 12 to differentiate between two situations. If no force is being applied because the patient is not wearing the appliance, the switch 38 is open. This records a first baseline value in device 12. When the appliance 10 is being worn, but the appliance 10 is not applying force to the patient's teeth, the switch 38 is closed. This records a second baseline such that, when force is applied by the headgear appliance 10, the force values are recorded upward from the second baseline. The use of two baselines allows all data to be recorded on a single channel recorder. The orthodontist can readily evaluate the force applied to the patient's teeth, the effect of that force, the time over which the force was applied and the patient compliance (i.e., how much the patient wore the headgear).

Although specific constructions have been presented herein, it is to be understood that these are for illustrative purposes only. Various modifications and adaptations will be apparent to those of skill in the art. For example, the potentiometer could be replaced with a magnetic (Hall effect device) or capacitance motion detector, which would be non-contact and not add frictional resistance to the movement of the strap 14. In view of possible modifications, it will be appreciated that the scope of the present invention should be determined by reference to the claims appended hereto.

We claim:

1. A removable orthodontic appliance comprising:
   at least one force applicator operable to exert extra-oral, corrective forces on teeth;
   a data storage device operably connected to store data corresponding to force applied by the force applicator; and
   a potentiometer operably connected to the force applicator such that a resistance across two terminals of the potentiometer depends on the force being applied by the force applicator, the potentiometer being operably connected to supply a force signal to the data storage device such that the data storage device stores data corresponding to force applied by the force applicator.

2. The appliance of claim 1 wherein the potentiometer is a slide potentiometer having a slide member that moves dependent on the force applied by the force applicator.

3. The appliance of claim 2 wherein the force applicator is a first spring and the first spring is linked to the slide member such that the slide member moves dependent on the spring position.

4. The appliance of claim 3 further comprising a second spring for applying the extra-oral, corrective forces.

5. The appliance of claim 3 wherein the first spring is biased in compression for applying the extra-oral, corrective forces.

6. The appliance of claim 3 further comprising a switch operably connected between the data storage device and the potentiometer, wherein the switch has a state dependent on whether the appliance is being worn by a patient, and wherein the state of the switch allows the data storage device to record patient compliance data indicating whether a patient is wearing the appliance.

7. The appliance of claim 6 wherein the switch is in a closed state when the appliance is being worn by a patient and wherein the switch is in an open state when the appliance is not being worn by a patient.

8. The appliance of claim 6 wherein the switch is a bending switch that senses whether the appliance is on a patient by sensing whether it is bent.

9. The appliance of claim 1 further comprising a switch operably connected between the data storage device and the potentiometer, wherein the switch has a state dependent on whether the appliance is being worn by a patient, and wherein the state of the switch allows the data storage device to record patient compliance data indicating whether a patient is wearing the appliance.

10. The appliance of claim 9 wherein the switch is in a closed state when the appliance is being worn by a patient and wherein the switch is in an open state when the appliance is not being worn by a patient.

11. The appliance of claim 10 wherein the switch is a bending switch that senses whether the appliance is on a patient by sensing whether it is bent.

12. A removable orthodontic appliance comprising:
    at least one force applicator operable to exert extra-oral, corrective forces on teeth;
    a data storage device operably connected to store data corresponding to force applied by the force applicator;
    a force measurer operably connected to the force applicator and operably connected to supply a force signal to the data storage device such that the data storage device stores data corresponding to force applied by the force applicator; and
    a switch operably connected between the data storage device and the force measurer, wherein the switch has a state dependent on whether the appliance is being worn by a patient, and wherein the state of the switch allows the data storage device to record patient compliance data indicating whether a patient is wearing the appliance said switch being a bending switch that senses whether the appliance is on a patient by sensing whether it is bent.

13. The appliance of claim 12 wherein the switch is in a closed state when the appliance is being worn by a patient and wherein the switch is in an open state when the appliance is not being worn by a patient.

14. The appliance of claim 12 wherein the force applicator is a first spring and the first spring is linked to move part of the force measurer.

15. The appliance of claim 14 further comprising a second spring for applying the extra-oral, corrective forces.

16. The appliance of claim 14 wherein the force measurer is a slide potentiometer having a slide and the slide is the part linked to the first spring, and wherein a resistance across two terminals of the potentiometer depends on the force being applied by the first spring, the potentiometer being operably connected to supply a force signal to the data storage device such that the data storage device stores data corresponding to force applied by the first spring.

17. The appliance of claim 12 wherein the force measurer is a potentiometer and wherein a resistance across two terminals of the potentiometer depends on the force being applied by the force applicator.

18. The appliance of claim 17 wherein the potentiometer is a slide potentiometer having a slide and the slide is linked to move with the force applicator.

19. The appliance of claim 18 wherein the switch is a bending switch that senses whether the appliance is on a patient by sensing whether it is bent.

* * * * *